United States Patent
Fard

[19]

[11] Patent Number: 5,817,076

[45] Date of Patent: Oct. 6, 1998

[54] TOILET TRAINING DIAPERS

[76] Inventor: Safieh Bahramian Fard, P.O. Box 5164, Laguna Beach, Calif. 92651

[21] Appl. No.: 805,278

[22] Filed: Feb. 25, 1997

[51] Int. Cl.$^6$ .............................. A61F 13/15; A61F 13/20
[52] U.S. Cl. .............................................................. 604/361
[58] Field of Search .............................. 604/361, 385.1, 604/362

[56] References Cited

U.S. PATENT DOCUMENTS

| 2,127,538 | 8/1938 | Seiger | 604/361 |
| 4,356,818 | 11/1982 | Macias et al. | 604/361 |
| 4,704,108 | 11/1987 | Okada et al. | 604/361 |
| 5,264,830 | 11/1993 | Kline et al. | 604/361 |
| 5,291,181 | 3/1994 | DePonte | 604/361 |
| 5,395,358 | 3/1995 | Lu | 604/361 |
| 5,570,082 | 10/1996 | Mahgerefteh et al. | 604/361 |

*Primary Examiner*—John G. Weiss
*Assistant Examiner*—Ki Yong O
*Attorney, Agent, or Firm*—Charles C. H. Wu

[57] ABSTRACT

A toilet training diaper having a moisture sensory device embedded therein; said sensory device includes a control device, an energy source, and a sound or light emitting device. A dissolvable device that is sensitive to moisture is placed inside the sensor. Upon reaching certain threshold level of moisture, the dissolvable device disintegrates and causes energy to flow into the control device. The control device then activates a sound or lighting emitting device and alerts the user. The result is that both the wearer of the diaper and persons other than the wearer would be alerted to the fact that the diaper is soiled. This mechanism for alerting the wearer and persons other than the wearer of the diaper can be used as a part of a training system to prevent or reduce toiling problems.

18 Claims, 2 Drawing Sheets

TOILET TRAINING DIAPERS

BACKGROUND OF THE INVENTION

The present invention relates to a toilet training diaper. Specifically, a diaper with a sensory device embedded inside. Upon detection of changes in moisture, the sensory device emits a signal in the form of sound or light detectable to human.

There are many reasons why one would want a toilet training diaper. Firstly, soiling and wetting problems for children and elderly cause embarrassment and extra laundering chores. Thus, the toilet training diaper can be used as a behavior treatment tool to cut down or eliminate soiling and wetting problems for children and elderly. Conceivably, the toilet training diaper can be used in conjunction with a positive reinforcement, positive practice and cleanliness training.

Secondly, the toilet training diaper can assist in the maintenance of the basic cleanliness and hygiene of children or elderly. Upon detection of wetness, the toilet training diaper emits a signal to allow the caretaker to know that diaper needs to be changed. Timely change of diapers will ensure that the user of the diaper will have a dry and healthy skin maintain a certain comfort level.

Thus, there is a need for a toilet training diaper.

SUMMARY OF THE INVENTION

The present invention meets these needs by providing a sensory device that is self contained and compact enough for embedding inside of a diaper or a similar type of clothing. In one aspect of the invention, the sensor is powered by a tiny battery similar to the type used in hearing aids or singing holiday greeting cards. The sensor includes a moisture detection mechanism, means for emitting a sound signal, and means for emitting a light signal.

The sensor further includes means for attaching the sensor to the diaper. The attaching means is capable of withstanding human movements so that the sensor will stay affixed to the diaper and will not be separated from the diaper.

In another aspect of the invention, the sensor can be powered by chemical energy rather than by electrical battery. Chemical energy cell stored inside the sensor releases energy to a sounding device and a lighting device upon detection of changes in moisture.

BRIEF DESCRIPTION OF THE DRAWINGS

These and other features, aspects, and, advantages of the present invention will become better understood with reference to the following description, appended claims, and accompanying drawings, where:

DESCRIPTION OF THE PREFERRED EMBODIMENT

Figure 1:
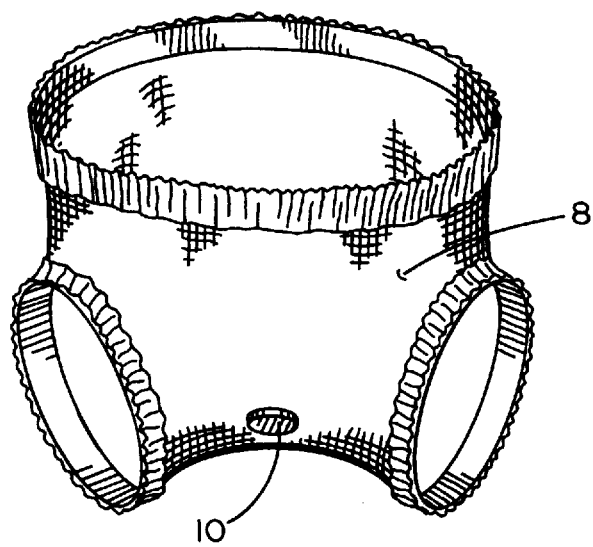
FIG. 1 is a side view of the toilet training diaper having a sensor placed within the diaper according to the present invention.
Figure 1:
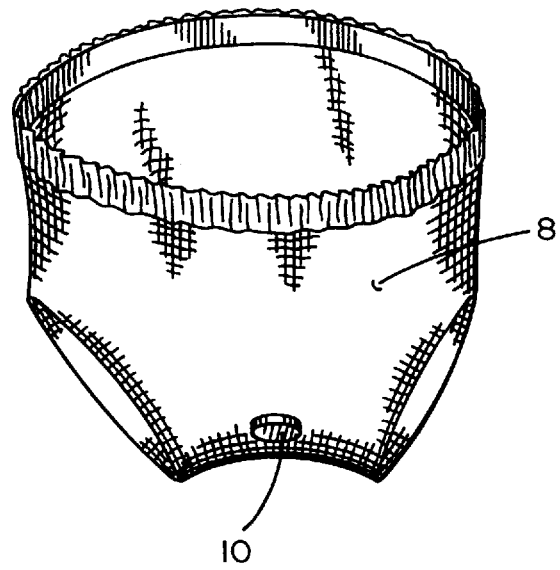
Figure 2:
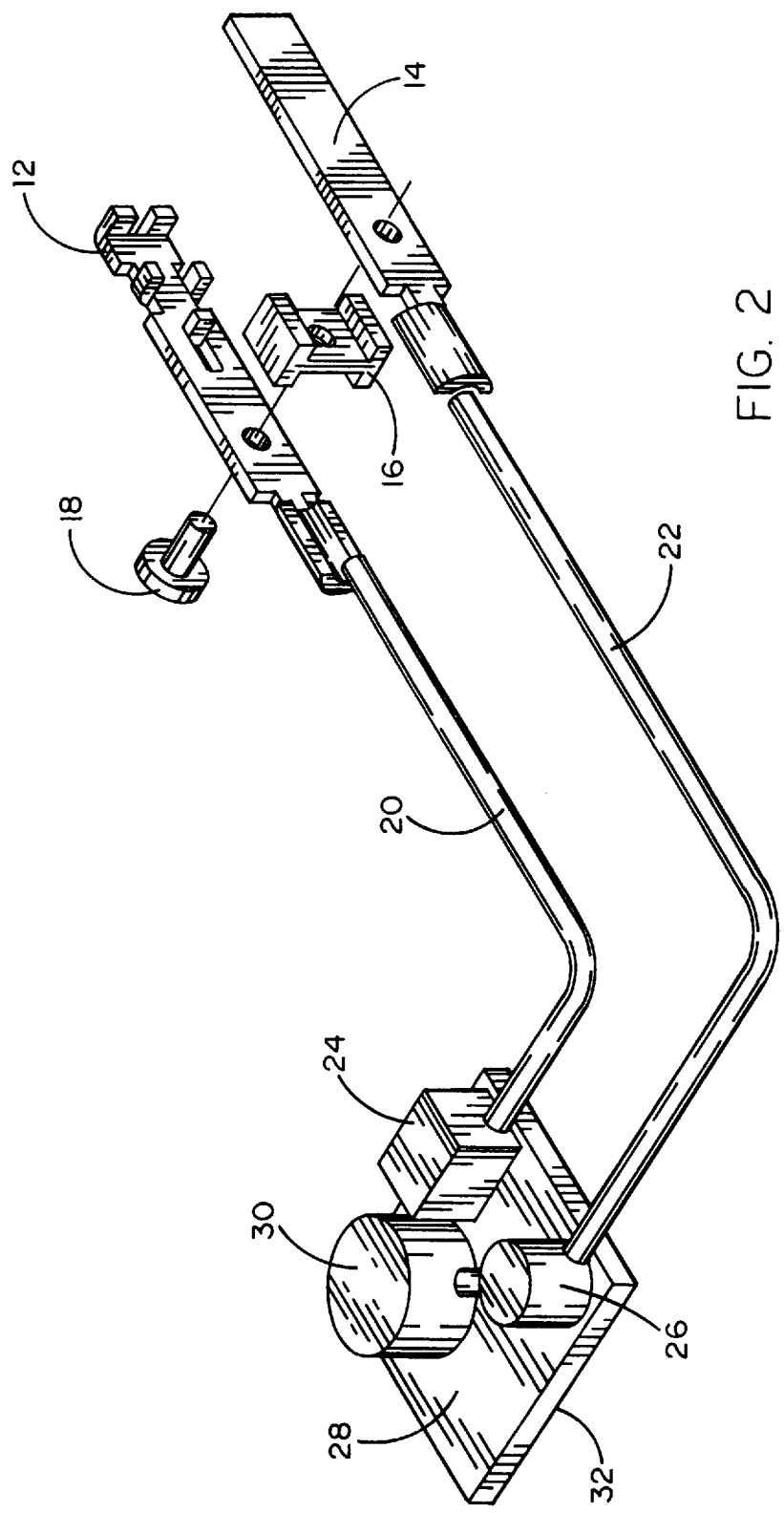
FIG. 2 is a detail view of the sensor device of FIG. 1.

The present invention is directed to toilet training diaper having a moisture sensory device embedded therein. The sensor is particularly suitable for detecting moisture of a diaper. With references to FIGS. 1 and 2 of the drawings, a diaper type of clothing 8 having a sensor 10 embedded therein. The sensor 10 consists of a mounting plate 28 having a battery 26, a control unit 24, and a sound emitting device 30 attached thereto. The mounting plate having an attaching means 32 for attaching the mounting plate to the diaper type clothing.

The control unit 24 is being connected to an upper spring plate 12 through an upper spring cable 20. The battery 26 is being connected to a lower spring plate 14 through a lower spring cable 22.

A dissolvable separator 16 is located between the upper spring plate 12 and the lower spring plate 14. A pin 18 holds and align the dissolvable separator 16 between the upper spring plate 12 and the lower spring plate 14.

The control unit 24 controls the activation of the sound emitting device 30. Upon reaching a certain threshold of moisture level, the dissolvable separator 16 disintegrates and causes the upper spring plate 12 to make contact with the lower spring plate 14. After the upper spring plate 12 and the lower spring plate 14 are in contact, electrical current flows from the battery 26 and into the control unit 24. The control unit 24 senses the electrical current and activates the sound emitting device 30.

Although the present invention has been described in considerable detail with reference to certain preferred versions thereof, other versions are possible. For example, a light emitting device can be used instead of a sound emitting device 30. Also, the control unit 24 and the sound emitting device 30 can be integrated into a one unit using integrated circuit technology. Similarly, the battery 26 can be integrated with the control unit 24 and the sound emitting device 30.

In addition, the battery 26 can be replaced with a chemical or light based energy. For example, photo cells can be utilized as means of storing and releasing energy when the device is not being used.

Therefore, the spirit and scope of the appended claims should not necessarily be limited to the description of the preferred versions contained herein.

What is claimed is:

1. A toilet training diaper comprising:
   (a) a diaper type clothing having a moisture sensor embedded therein;
   (b) said moisture sensor having a housing, a mounting plate, said mounting plate having two sides, one side having a means attachable to the diaper type clothing, the other side is configured with a smooth surface to allow mounting of electronic devices;
   (c) a battery is attached to said smooth surface of the mounting plate;
   (d) a sound emitting device attached to said smooth surface of the mounting plate;
   (e) a control unit attached to said mounting plate;
   (f) an upper spring plate having a hole and two ends, one end is configured to be attachable to a cable, the other end is configured to the shape of a male receptacle;
   (g) a lower spring plate having a hole and two ends, one end is configured to be attachable to a cable, the other end is configured to receive the male receptacle end of the upper spring plate;
   (h) an upper spring cable having two ends, one end of the upper spring cable is connected to the control device, the other end is connected to the upper spring plate, the upper spring cable is a conductor;
   (i) a lower spring cable having two ends, one end of the lower spring cable is connected to the battery, the other end is connected to the lower spring plate, the lower spring cable is a conductor;

(j) a dissolvable separator having a hole bore at its center is placed between the upper spring plate and the lower spring plate; and (k) a pin having a diameter less than the diameter of the hole of the upper spring plate and the diameter of the hole of the lower spring plate is disposed in the hole of the upper spring plate, the hole of the dissolvable separator, and the hole of the lower spring plate.

2. The toilet training diaper of claim 1, wherein the upper spring cable is a conductor.

3. The toilet training diaper of claim 1, wherein the lower spring cable is a conductor.

4. The toilet training diaper of claim 1, wherein the upper spring plate is made of tin.

5. The toilet training diaper of claim 1, wherein the lower spring plate is made of tin.

6. The toilet training diaper of claim 1, wherein the pin is made of nylon.

7. The toilet training diaper of claim 1, wherein the sound emitting device is capable of emitting light.

8. A toilet training diaper comprising:

(a) a diaper type clothing having a moisture sensor embedded therein;

(b) said moisture sensor having a housing, a mounting plate, said mounting plate having two sides, one side having a means attachable to the diaper type clothing, the other side is configured with a smooth surface to allow mounting of electronic devices;

(c) a battery is attached to said smooth surface of the mounting plate;

(d) a sound emitting device attached to said smooth surface of the mounting plate;

(e) a control unit attached to said mounting plate;

(f) an upper spring plate having a hole and two ends, one end is configured to be attachable to a cable, the other end is configured to the shape of a male receptacle;

(g) a lower spring plate having a hole and two ends, one end is configured to be attachable to a cable, the other end is configured to receive the male receptacle end of the upper spring plate;

(h) an upper spring cable having two ends, one end of the upper spring cable is connected to the control device, the other end is connected to the upper spring plate, the upper spring cable is a conductor;

(i) a lower spring cable having two ends, one end of the lower spring cable is connected to the battery, the other end is connected to the lower spring plate, the lower spring cable is a conductor;

(j) a dissolvable separator having a hole bore at its center is placed between the upper spring plate and the lower spring plate; and (k) a pin having a diameter less than the diameter of the hole of the upper spring plate and the diameter of the hole of the lower spring plate is disposed in the hole of the upper spring plate, the hole of the dissolvable separator, and the hole of the lower spring plate.

9. The toilet training diaper of claim 8, wherein the upper spring plate is made of tin.

10. The toilet training diaper of claim 8, wherein the lower spring plate is made of tin.

11. The toilet training diaper of claim 8, wherein the pin is made of nylon.

12. The toilet training diaper of claim 8, wherein the sound emitting device is capable of emitting light.

13. A toilet training diaper comprising:

(a) a diaper type clothing having a moisture sensor embedded therein;

(b) said moisture sensor having a housing, a mounting plate, said mounting plate having two sides, one side having a means attachable to the diaper type clothing, the other side is configured with a smooth surface allowing mounting of electronic devices;

(c) a battery with a photocell is attached to said smooth surface of the mounting plate;

(d) a sound emitting device attached to said smooth surface of the mounting plate;

(e) a control unit attached to said mounting plate;

(f) an upper spring plate having a hole and two ends, one end is configured to be attachable to a cable, the other end is configured to the shape of a male receptacle;

(g) a lower spring plate having a hole and two ends, one end is configured to be attachable to a cable, the other end is configured to receive the male receptacle end of the upper spring plate;

(h) an upper spring cable having two ends, one end of the upper spring cable is connected to the control device, the other end is connected to the upper spring plate;

(i) a lower spring cable having two ends, one end of the lower spring cable is connected to the battery, the other end is connected to the lower spring plate;

(j) a dissolvable separator having a hole bored at its center is placed between the upper spring plate and the lower spring plate; and (k) a pin having a diameter less than the diameter of the hole of the upper spring plate and the diameter of the hole of the lower spring plate is disposed in the hole of the upper spring plate, the hole of the dissolvable separator, and the hole of the lower spring plate.

14. The toilet training diaper of claim 13, wherein the upper spring cable is a conductor.

15. The toilet training diaper of claim 13, wherein the lower spring cable is a conductor.

16. The toilet training diaper of claim 13, wherein the upper spring plate is made of tin.

17. The toilet training diaper of claim 13, wherein the lower spring plate is made of tin.

18. The toilet training diaper of claim 13, wherein the pin is made of nylon.

* * * * *